US011956226B2

(12) United States Patent
Teeple et al.

(10) Patent No.: US 11,956,226 B2
(45) Date of Patent: Apr. 9, 2024

(54) MEDICAL RECORDS ACCESS SYSTEM

(71) Applicant: Evernorth Strategic Development, Inc., St. Louis, MO (US)

(72) Inventors: Jason Teeple, Doylestown, PA (US); Baird Kaake, Wethersfield, CT (US)

(73) Assignee: Evernorth Strategic Development, Inc., St. Louis, MO (US)

( * ) Notice: Subject to any disclaimer, the term of this patent is extended or adjusted under 35 U.S.C. 154(b) by 389 days.

(21) Appl. No.: 17/388,101

(22) Filed: Jul. 29, 2021

(65) Prior Publication Data

US 2023/0029634 A1    Feb. 2, 2023

(51) Int. Cl.
*H04L 9/40*        (2022.01)
*G16H 10/60*       (2018.01)
*G16H 30/20*       (2018.01)

(52) U.S. Cl.
CPC .......... *H04L 63/083* (2013.01); *G16H 10/60* (2018.01); *G16H 30/20* (2018.01); *H04L 63/102* (2013.01)

(58) Field of Classification Search
CPC ..... H04L 63/083; H04L 63/102; G16H 10/60; G16H 30/20
See application file for complete search history.

(56) References Cited

U.S. PATENT DOCUMENTS

| 6,957,268 | B1 * | 10/2005 | Odom ..................... H04L 67/06 370/231 |
| 7,100,197 | B2 | 8/2006 | Rail |
| 7,448,047 | B2 | 11/2008 | Poole |
| 7,707,627 | B2 | 4/2010 | Hirsh |
| 7,752,289 | B2 | 7/2010 | Kikkawa |
| 8,826,021 | B2 | 9/2014 | Savage |
| 9,686,674 | B2 | 6/2017 | Lin |
| 9,787,692 | B2 | 10/2017 | Peleg |
| 9,854,431 | B2 | 12/2017 | Lin |
| 10,027,654 | B2 | 7/2018 | Bringer |
| 10,340,036 | B2 * | 7/2019 | Takahashi .............. G16H 10/60 |
| 10,629,310 | B2 | 4/2020 | Livesay |
| 10,964,430 | B2 | 3/2021 | Willard |
| 11,107,563 | B2 | 8/2021 | Vogt |
| 11,277,497 | B2 * | 3/2022 | Johnson ................ H04L 9/3239 |

(Continued)

FOREIGN PATENT DOCUMENTS

| CN | 109671475 A | 4/2019 |
| CN | 110046186 A | 7/2019 |

(Continued)

*Primary Examiner* — Hosuk Song
(74) *Attorney, Agent, or Firm* — Schwegman Lundberg & Woessner, P.A.

(57) ABSTRACT

Methods and systems for performing operations comprising: receiving, by a server from a client device, a request to access a data object comprising one or more medical records, the request comprising authentication information; determining, by the server, that the authentication information is valid; in response to determining that the authentication information is valid, transferring, by the server, the data object to a temporary storage location; transmitting a first portion of the data object to the client device from the temporary storage location; and deleting the first portion of the data object from the temporary storage location after the first portion of the data object has been transmitted to the client device.

20 Claims, 6 Drawing Sheets

(56) References Cited

U.S. PATENT DOCUMENTS

| | | | |
|---|---|---|---|
| 11,570,180 B1 * | 1/2023 | Fitzpatrick | H04L 9/0643 |
| 2010/0054566 A1 * | 3/2010 | Toda | H04L 67/62 |
| | | | 705/3 |
| 2015/0347681 A1 | 12/2015 | Bartlett, II | |
| 2017/0180518 A1 | 6/2017 | Choi | |
| 2017/0270532 A1 | 9/2017 | Livesay | |
| 2018/0268417 A1 | 9/2018 | Livesay | |
| 2019/0034589 A1 | 1/2019 | Chen | |
| 2019/0034590 A1 | 1/2019 | Oren | |
| 2019/0103173 A1 | 4/2019 | Power | |
| 2019/0198181 A1 | 6/2019 | Livesay | |
| 2020/0251194 A1 | 8/2020 | Vogt | |
| 2020/0342455 A1 | 10/2020 | Poteet, III | |
| 2021/0090717 A1 * | 3/2021 | Manuel | G06F 16/955 |

FOREIGN PATENT DOCUMENTS

| | | |
|---|---|---|
| CN | 110691548 A | 1/2020 |
| CN | 113380351 A | 9/2021 |
| EP | 3362890 A | 8/2018 |
| EP | 3489958 A | 5/2019 |
| EP | 3634204 A | 4/2020 |
| EP | 3799056 A | 3/2021 |
| KR | 101575146 B1 | 12/2015 |
| KR | 20200003407 A | 1/2020 |
| WO | 2019022779 A1 | 1/2019 |

* cited by examiner

MEDICAL RECORDS ACCESS SYSTEM

BACKGROUND

Users are increasingly using the Internet, such as websites, to access information and perform transactions. As more and more services become available over the Internet, wider access to information is required. Providing seamless access to a wide variety of information, including medical records, becomes critical to allowing users to perform everyday tasks.

DETAILED DESCRIPTION

Figure 1:
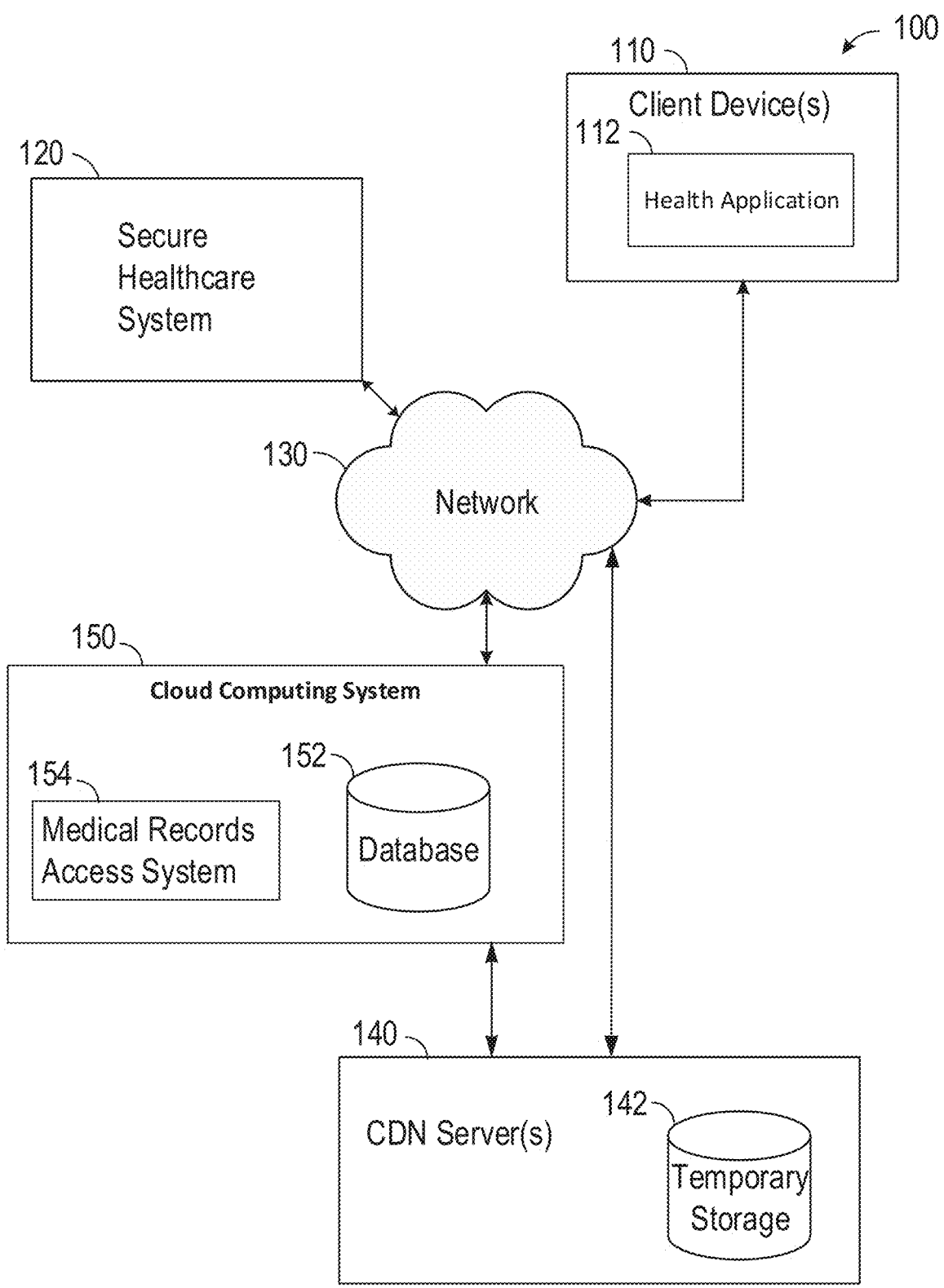
FIG. 1 is a block diagram of an example medical records access system, according to some embodiments.

Example methods and systems for a medical records access system are described. In the following description, for purposes of explanation, numerous specific details are set forth in order to provide a thorough understanding of example embodiments. It will be evident, however, to one of ordinary skill in the art that embodiments of the invention may be practiced without these specific details.

Typical systems use cloud computing systems to provide storage and computing resources. Cloud computing systems are configured to allocate a certain quantity of available storage space and computing resources on an on-demand basis at varying costs. In some examples, a secure healthcare entity can expose one or more of its services to various individuals by leveraging the cloud computing systems. This can reduce various startup and operation costs associated with running the secure healthcare entity processes. While operating a service using the cloud computing systems generally works well, such systems have some limitations. One limitation associated with operating services using a cloud computing system is the resource restrictions imposed by such cloud computing systems. Specifically, the cloud computing system can impose a file size transfer limit that does not allow (prevents) file sizes larger than a specified amount (e.g., 6 megabytes (MB)) to be transferred over the network. Under ordinary circumstances, this limitation does not impact operating the services on the cloud computing systems. However, in the case of medical records, such a limitation on the file size transfer severely restricts the amount and type of information that can be provided to end users or patients. This is mainly attributed to the fact that medical records usually include file sizes that are larger than the file size transfer limit (6 MB) in some cases by one or more orders of magnitude.

The disclosed embodiments provide systems and methods for enabling a secure healthcare entity to provide services using a cloud computing system and for providing end users with access to large medical files, such as files that exceed 6 MB in size. Specifically, the secure healthcare entity can enable a client device to operate a third-party health or healthcare application to retrieve and access a given patient's medical records. The secure healthcare entity can operate the storage and processing resources on the cloud computing system. Namely, the secure healthcare entity can use the cloud computing system to provide authentication information, such as authentication tokens, to the third-party health application. When one or more medical records are requested by the client device via the health application, the request can be routed to a content delivery network (CDN) for retrieval of the medical record instead of retrieving the medical records from the cloud computing system. Specifically, because the medical records can exceed the file size transfer limit imposed by the cloud computing system, a separate CDN server(s) can be utilized to complete such a transfer.

In an example, the request for the medical records can be provided from the client device to the CDN server along with authentication information. The CDN server can verify validity of the authentication information and, if such information is valid, the CDN server can load the medical record files onto a temporary storage location. Storing the medical record files temporarily in the temporary storage location enhances security of the medical records. The CDN server may not have any file size transfer limits and can thus satisfy the request for the one or more medical records. Specifically, the CDN server can transmit the medical records or a specific portion of the medical records that is requested to the client device and then can immediately delete the transferred information from the temporary storage location. In some cases, the CDN server can automatically delete the temporary storage location after a threshold time period elapses. The CDN server can only retain those medical records in the temporary storage location that have yet to be requested by the health application implemented by the client device.

In this way, the secure healthcare entity service can leverage the cloud computing system to run its services without being hamstrung by the file size transfer limits imposed by the cloud computing system. This allows resources of a server to be utilized more efficiently which improves the quality of service an end user experiences.

FIG. 1 is a block diagram showing an example system 100 according to various exemplary embodiments. The system 100 includes one or more client devices 110, a secure healthcare system 120, a cloud computing system 150, and one or more CDN servers 140 that are communicatively coupled to each other over a network 130 (e.g., Internet, telephony network).

As used herein, the term "client device" refers to any machine that interfaces to a communications network (such as network 130) to access medical records associated with a patient, such as from the cloud computing system 150 or the CDN servers 140. The client device 110 may be, but is not limited to, a mobile phone, desktop computer, laptop, portable digital assistant (PDA), smart phone, a wearable device (e.g., a smart watch), tablet, ultrabook, netbook, laptop, multi-processor system, microprocessor-based or programmable consumer electronic, game console, set-top box, or any other communication device that a user may use to access a network or a service hosted by the cloud computing system 150 or the CDN servers 140.

The network 130 may include, or operate in conjunction with, an ad hoc network, an intranet, an extranet, a virtual private network (VPN), a local area network (LAN), a wireless network, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, fifth generation wireless (5G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The secure healthcare system 120 can be any entity or service that manages healthcare related information (e.g., medical records) for a plurality of patients. The medical records or healthcare related information can include pharmacy claims, medical data, laboratory data, magnetic resonance (MR) imaging, ultrasound imaging, X-Ray imaging, DICOM files, and so forth.

In one example, the secure healthcare system 120 can be part of a pharmacy benefit manager. The secure healthcare system 120 can interface with a variety of medical sources, such as physician offices, hospitals, pharmacies and so forth to collect and aggregate the healthcare related information for many patients. The secure healthcare system 120 can operate its services using resources, such as storage and processing resources, provided by a cloud computing system 150. In some cases, the secure healthcare system 120 can store certain medical records that are greater than a given size (e.g., greater than 6 MB) on one or more CDN servers 140. Specifically, as the secure healthcare system 120 can collect the medical records for a group of patients, the secure healthcare system 120 can determine whether a file size of the medical records or a file type associated with the medical records meets a criterion. In response to determining that the file size of the medical records or file type meets the criterion, the secure healthcare system 120 can store the files on the CDN servers 140 instead of on the cloud computing system 150. The secure healthcare system 120 can store identifiers of the medical records that are stored on the CDN servers 140 on a database 152 of the cloud computing system 150.

In some implementations, the client device 110 can host one or more applications, such as a health application 112. The health application 112 can be an application, installed on the client device 110, that allows a user or patient to search for and browse medical records associated with the patient or user. The health application 112 can be provided by a third-party relative to an entity that operates or provides the secure healthcare system 120 and/or the CDN servers 140. In other implementations, the health application is provided by the secure healthcare system 120. The health application 112 can be configured to obtain authentication information from the secure healthcare system 120, such as in accordance with an OATH 2 authentication protocol. To do so, the health application 112 can provide various secure information (e.g., patient name, date of birth, social security number, username, password, or any combination thereof) to the secure healthcare system 120 over the network 130. After the secure healthcare system 120 receives the secure information from the health application 112 and verifies the authenticity of the patient or user of the health application 112, the secure healthcare system 120 can generate an authentication token for the health application 112.

The authentication token can be time limited such that the authentication token expires and needs to be renewed after a specified time period (e.g., 24 hours or 30 days). The secure healthcare system 120 can associate the authentication token with user information associated with the patient and provides the authentication token back to the health application 112. In an example, the secure healthcare system 120 can communicate with the cloud computing system 150 to generate the authentication token. Namely, the cloud computing system 150 can use processing resources to generate the authentication token. The cloud computing system 150 can provide the authentication token directly to the health application 112 or can provide the authentication token to the health application 112 via the secure healthcare system 120.

In some implementations, in response to generating the authentication token, the secure healthcare system 120 can identify one or more medical records associated with the patient. The secure healthcare system 120 can instruct the CDN servers 140 to prepare such medical records for transmission to the health application 112. For example, the secure healthcare system 120 can identify one or more medical records that satisfy a file size or file type criterion and instructs the CDN server 140 to generate a uniform resource locator (URL) for such medical records. The CDN servers 140 can transfer the identified one or more medical records to a temporary storage 142. The CDN servers 140 can provide the URL that identifies the temporary storage 142 in which the identified one or more medical records are stored back to the secure healthcare system 120. The temporary storage 142 can be an ephemeral storage location that is automatically deleted when certain one or more criteria is met. The criteria can include an access pattern or a time. For example, the criteria can specify that a given medical record stored in the temporary storage 142 is automatically deleted within a threshold period of time (e.g., 50 seconds) of being accessed or after the medical record is retrieved a certain quantity of times (e.g., 2 times). In another example, the criteria can specify that all contents in the temporary storage 142 is deleted automatically after a specified time period (e.g., after 72 hours).

In some implementations, the secure healthcare system 120 can then provide a list of the identified medical records to the health application 112 together with the associated URL. The health application 112 can display a list of the identified medical records in a user interface for the user to select for retrieval and viewing. The health application 112 can receive a user selection of a given medical record that is displayed by the user interface. In response, the health application 112 can retrieve the URL associated with the selected medical record and provides the previously received authentication token to the CDN servers 140 along with the URL to retrieve the medical record. The CDN servers 140 can process the authentication information to verify its authenticity or determine that the authentication information is valid. In some cases, the CDN servers 140 can apply one or more rules to the authentication information to determine its validity. In an example, the CDN servers 140 can retrieve an issuer identifier that is contained in the authentication information. The CDN servers 140 can compare the issuer identifier (identity information) with a predetermined list of known issuer identifiers. In response to determining that the issuer identifier (identity information) matches an issuer stored in the predetermined list, the CDN servers 140 can enable access to the content stored at the URL provided by the health application 112.

In some implementations, the secure healthcare system 120 can provide a list of the identified medical records to the health application 112 without the associated URL. In particular, the secure healthcare system 120 can store the URL of the associated medical records in the database 152 of the cloud computing system 150. The health application 112 can display a list of the identified medical records in a user interface for the user to select for retrieval and viewing. The health application 112 can receive a user selection of a given medical record that is displayed by the user interface. In response, the health application 112 can communicate the identification of the selected medical record to the medical records access system 154. The medical records access system 154 can identify the associated URL stored on the database 152 of the selected medical record. The medical records access system 154 can then retrieve the URL associated with the selected medical record and provides the URL to the health application 112. The health application 112 can then provide the previously received authentication token to the CDN servers 140 along with the URL to retrieve the medical record. The CDN servers 140 can process the authentication information to verify its authenticity or determine that the authentication information is valid. In some cases, the CDN servers 140 can apply one or more rules to the authentication information (identity information contained in the authentication information such as, patient name, username, social security information, issuer information, and so forth) to determine its validity. In an example, the CDN servers 140 can retrieve an issuer identifier from the authentication information. The CDN servers 140 can compare the issuer identifier with a predetermined list of known issuer identifiers. In response to determining that the issuer identifier is stored in the predetermined list, the CDN servers 140 can enable access to the content stored at the URL provided by the health application 112.

For example, the CDN servers 140 can retrieve the selected medical record from the temporary storage 142 identified by the URL and transmit the retrieved medical record back to the health application 112. In some implementations, the CDN servers 140 can automatically delete the retrieved medical record from the temporary storage 142 in response to transmitting the medical record to the health application 112. The health application 112 can then store the medical record locally on a storage device of the client device 110. The health application 112 can then present the contents of the medical record to a patient or user of the client device 110 in response to receiving a request to view the medical record.

In some embodiments, the CDN servers 140 can transfer the medical records to the temporary storage 142 in response to receiving a request for accessing the medical records. Namely, the CDN servers 140 can receive a request from the client device 110 to access the medical records based on a document reference URL. The CDN servers 140 can then transfer the medical records to the temporary storage 142 to enable the health application 112 to access the medical records. In such implementations, the health application 112 after obtaining the authentication token from the secure healthcare system 120, can present a list of medical records associated with the patient or user. The health application 112 can receive a user selection of a given medical record from the list. The health application 112 can communicate the identification of the given medical record to the cloud computing system 150 (e.g., via an Application Programming Interface (API) and/or a cloud computing gateway) of the cloud computing system 150. The cloud computing system 150 can access the medical records access system 154 to determine whether the identified medical record is locally stored on the storage resources (e.g., database 152) of the cloud computing system 150 or if the medical record is stored offsite on one or more CDN servers 140.

In response to determining that the medical record is stored in the cloud computing system 150 resources (e.g., if the medical record is sufficiently small in size that it does not violate (does not exceed) any file transfer restrictions, file size transfer limits, imposed by the API of the cloud computing system 150), the cloud computing system 150 can provide the requested medical record back to the health application 112. In response to determining that the requested medical record is not stored in the cloud computing system 150 resources (e.g., if the medical record is sufficiently large in size that it does violate (exceeds) file transfer restrictions, file size transfer limits, imposed by the API of the cloud computing system 150), the cloud computing system 150 can retrieve a URL or uniform resource identifier (URI) of the requested medical record from the database 152. The cloud computing system 150 can provide the URL or URI to the health application 112. In some cases, the cloud computing system 150 can provide the URL or URI of all the medical records associated with the authentication token or patient and not only the requested medical record. Each medical record can be associated with a different URL or URI.

The health application 112 can transmit, along with authentication information, a request for the records associated with the URL or URI (received from the cloud computing system 150) to the CDN servers 140. The CDN servers 140 can verify whether the authentication information is valid and in response to determining that the authentication information is valid, the CDN servers 140 can transfer or move the requested medical records to the temporary storage 142 from a persistent secure storage location. In some cases, the CDN servers 140 can also move other records associated with the patient and not only those that have been requested and associated with the URL or URI that is received. The CDN servers 140 can associate ephemeral properties with the temporary storage 142 so that the content stored in the temporary storage 142 is only temporarily available and is automatically deleted when certain one or more criteria is met. The CDN servers 140 can provide the selected medical records from the temporary storage 142 to the health application 112. The health application 112 can visually identify those medical records in a displayed list for which the corresponding files have been retrieved from the CDN servers 140 from those which have yet to be selected for retrieval from the CDN servers 140. The CDN servers 140 can automatically delete the medical records from the temporary storage 142 that have been transmitted to the health application 112. The CDN servers 140 can retain or not delete medical records stored in the temporary storage 142 that have yet to be requested for transmission to the health application 112. Such records may be automatically deleted without being requested after a certain period of time.

The CDN servers 140 can predictively load other medical records associated with a given patient into the temporary storage 142 based on the initial request for the medical record. Namely, the CDN servers 140 can apply one or more machine learning (ML) models to predict what other medical records or type of medical records a user or patient is likely to request based on the medical record being requested. The ML model can be trained to establish a relationship between a plurality of training medical record requests and a known set of medical records that are requested following the requests for the training medical record. Specifically, the ML model is trained to establish a relationship between a first type of medical record and one or more other types of medical records that are requested following request of the first type of medical record. In such cases, in response to receiving a request for a given type of medical record (e.g., an MR image of an anatomical feature), the ML model can predict that one or more other types of medical records (e.g., ultrasound images and lab results associated with the anatomical feature) will be requested. In such cases, the CDN servers 140 can load the requested given type of medical record into the temporary storage 142 and the other types of medical records that are predicted if they are available.

A machine learning model(s) training module can be provided to train one or more machine learning techniques based on sets of input-output pairs of paired training data sets. For example, the model training module may train the ML model parameters by minimizing a loss function based on one or more ground-truth medical record types that are selected by a pool of patients following request for a given type of medical record. The ML model can include any one or combination of classifiers or neural networks, such as an artificial neural network, a convolutional neural network, an adversarial network, a generative adversarial network, a deep feed forward network, a radial basis network, a recurrent neural network, a long/short term memory network, a gated recurrent unit, an auto encoder, a variational autoencoder, a denoising autoencoder, a sparse autoencoder, a Markov chain, a Hopfield network, a Boltzmann machine, a restricted Boltzmann machine, a deep belief network, a deep convolutional network, a deconvolutional network, a deep convolutional inverse graphics network, a liquid state machine, an extreme learning machine, an echo state network, a deep residual network, a Kohonen network, a support vector machine, a neural Turing machine, and the like.

Particularly, the ML model can be applied to a plurality of training medical record types features to estimate or generate a prediction of other types of medical records. In some implementations, a derivative of a loss function is computed based on a comparison of the estimated prediction of the other types of medical records and the ground truth medical records associated with the given type of medical record and parameters of the ML model are updated based on the computed derivative of the loss function.

In one example, the ML model receives a batch of training data that includes a first type of medical record and a corresponding set of other types of medical records that are requested following request for the first type of medical record. The ML model generates a feature vector based on the first type of medical record and generates a prediction of other types of medical records associated with the first type of medical record. The prediction is compared with the ground truth indication set of other types of medical records and parameters of the ML model are updated based on the comparison.

The result of minimizing the loss function for multiple sets of training data trains, adapts, or optimizes the model parameters of the corresponding ML models. In this way, the ML model is trained to establish a relationship between a first type of medical record and one or more other types of medical records that are requested following request of the first type of medical record.

After the machine learning model is trained, new data, including a new medical record type request is received. The trained machine learning technique may be applied to the new data to generate a prediction of other types of medical records that are likely to be requested following the new medical record type being requested. The predicted other types can then be loaded together with the new medical record type into the temporary storage 142.

Figure 2:
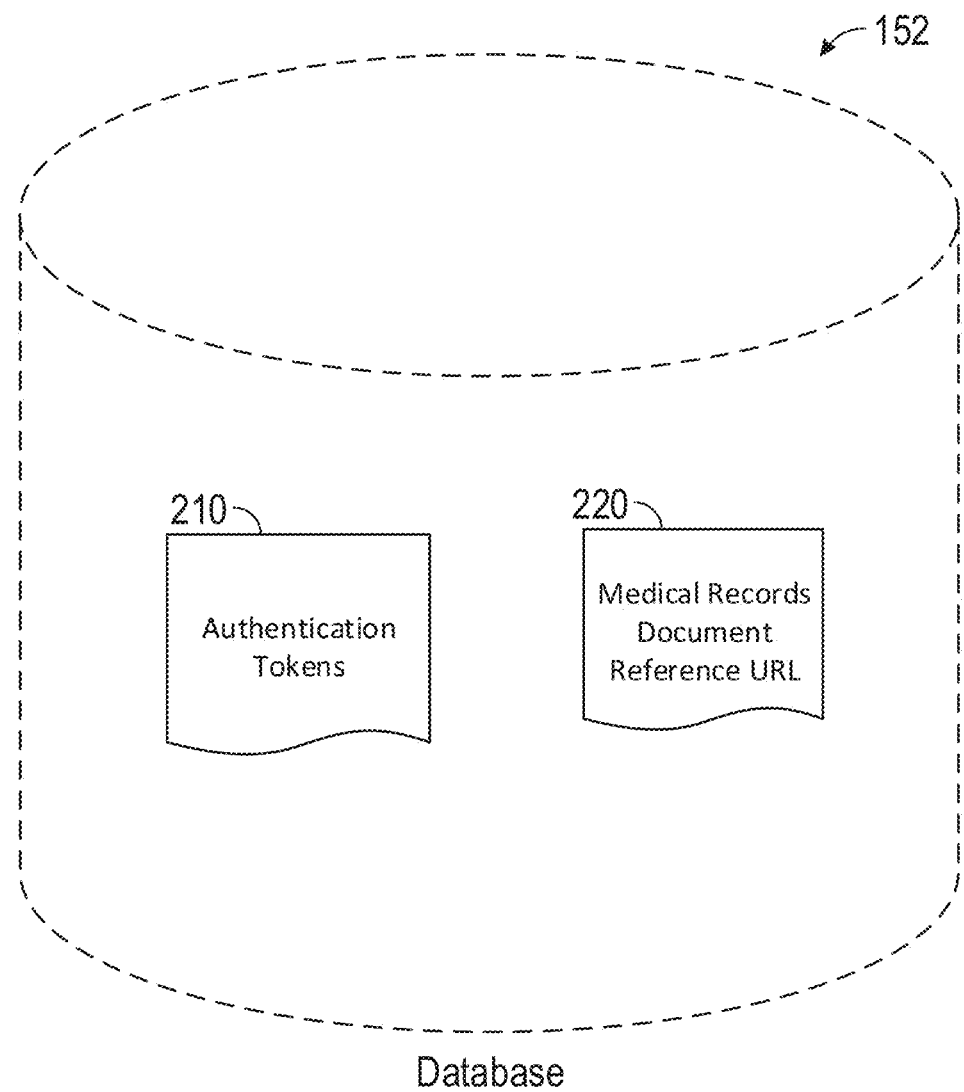
FIG. 2 is an example database that may be deployed within the system of FIG. 1, according to some embodiments.

FIG. 2 is an example database 152 that may be deployed within the system of FIG. 1, according to some embodiments. As shown, the database 152 includes authentication tokens 210 and the medical records document reference URL 220. The authentication tokens 210 stores a collection tokens generated based on requests for authentication by different health applications 112 of different patients. Each authentication token 210 can be associated with expiration criteria (e.g., date and time during which the token is valid). The medical records document reference URL 220 stores the references to medical records that are stored offsite in one or more CDN servers 140.

Figure 3:
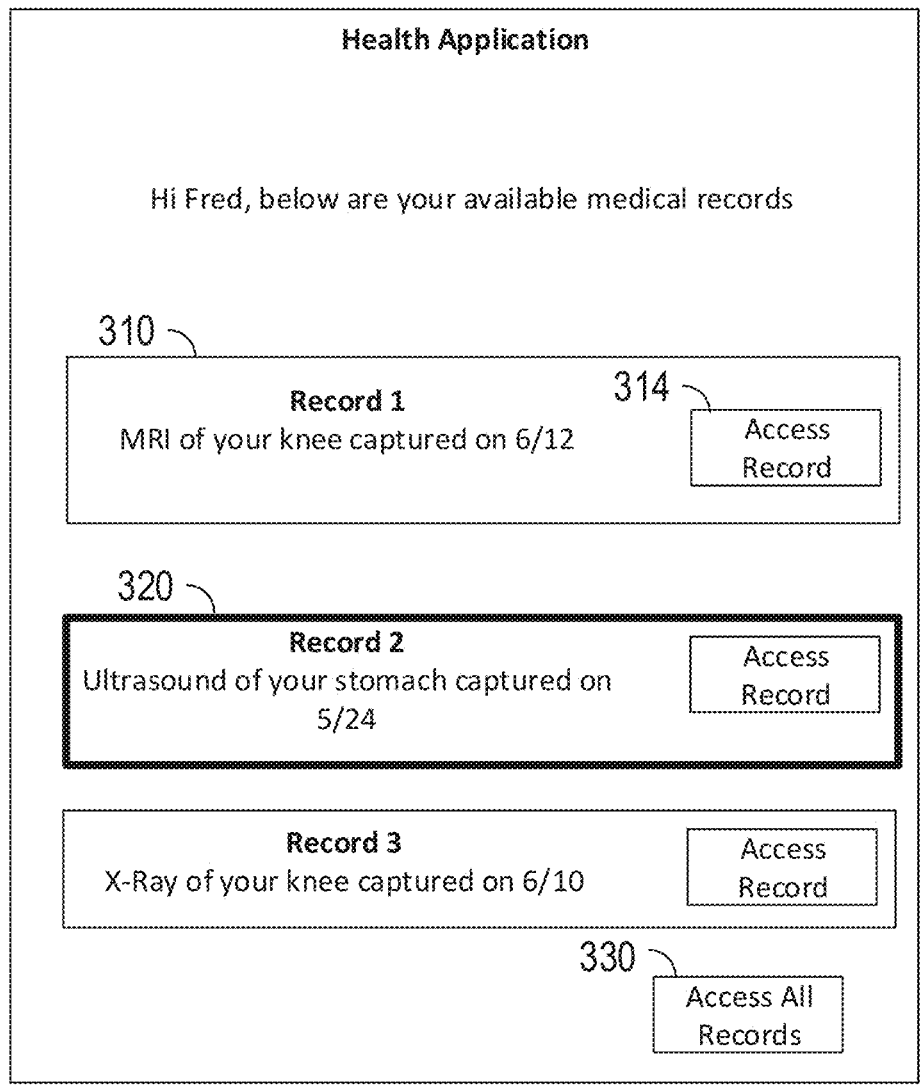
FIG. 3 is an example medical records access user interface generated by the system of FIG. 1, according to example embodiments.

FIG. 3 is an example medical records access user interface 300 generated by the system of FIG. 1, according to example embodiments. For example, the health application 112 can provide secure identifying information to the cloud computing system 150. The cloud computing system 150 can identify a list of medical records associated with the secure identifying information of the patient or user. The cloud computing system 150 can generate the authentication token and provide the authentication token along with the list of medical records back to the health application 112. The health application 112 can then generate for display the user interface 300 that lists the available medical records associated with the patient as received from the cloud computing system 150.

For example, the health application 112 can present a first medical record 310, such as an MR image of a knee captured on a given date. The first medical record 310 can include an access record option 314. In response to receiving a user selection of the access record option 314, the health application 112 can retrieve the URL of the corresponding first medical record 310 from local storage. Alternatively, the health application 112 can communicate with the cloud computing system 150 to retrieve the URL from the database 152. Once the URL is obtained by the health application 112, the health application communicates the URL to the CDN servers 140 along with the authentication information (e.g., authentication token).

The CDN servers 140 can transfer the corresponding medical record and, optionally, additional medical records associated with the patient to the temporary storage 142. The CDN servers 140 can transmit the medical records to the temporary storage 142 after verifying that the authentication information is valid. In some cases, the medical records may have been previously transferred to the temporary storage 142 prior to being requested by the health application 112. The CDN servers 140 can transmit the requested medical record from the temporary storage 142 to the health application 112 and automatically delete the medical record from the temporary storage 142 after transmitting the medical record to the health application 112. In some cases, the CDN servers 142 can trigger the automatic deletion of the medical record from the temporary storage 142 after a threshold period of time elapses since the request for the record is received from the health application 112. The threshold period of time can differ depending on the type of medical record being retrieved and can be determined based on historical access patterns of other users.

Once the health application 112 receives the medical record from the temporary storage 142, the health application 112 can visually distinguish the first medical record 310 from other medical records displayed in the user interface 300 for which the corresponding files have yet to be retrieved from the CDN servers 140. For example, the health application 112 can highlight or display an icon in association with the first medical record 310 to indicate that the underlying or associated medical file is locally stored and available to be viewed. A second medical record 320 may have not yet been selected to retrieve the corresponding medical file from the CDN servers 140. As such, the highlight or icon is not displayed in association with the second medical record 320. The health application 112 can receive a user selection of the first medical record 310 after the highlight or icon is displayed and can display the corresponding file. For example, the health application 112 can display the MR image retrieved from the CDN servers 140 in response to receiving the user selection of the first medical record 310.

In some cases, the health application can remove display of the access record option 314 in response to receiving the corresponding file from the CDN servers 140. In some cases, the health application 112 can only displays the access record option 314 for those medical records that have already been retrieved from the CDN servers 140. As an example, before the health application 112 can receive the medical record file from the CDN servers 140, the health application 112 can only display the medical record 310 without the access record option 314. In response to receiving a user selection of the medical record 310, the health application 112 can retrieve the medical record file from the CDN servers 140 and then can display the access record option 314. In response to then receiving a user selection of the access record option 314, the health application 112 can display the contents of the medical record file, such as in a new window or full screen.

The health application 112 can generate for display an access all records option 330. In response to receiving a user selection of the access all records option 330, the health application 112 communicates this selection along with the authentication information to the CDN servers 140. The CDN servers 140 can then transmit all the medical records stored in the temporary storage 142 to the health application 112. After transmitting all the medical records to the health application 112, the CDN servers 140 can delete the temporary storage 142.

Figure 4:
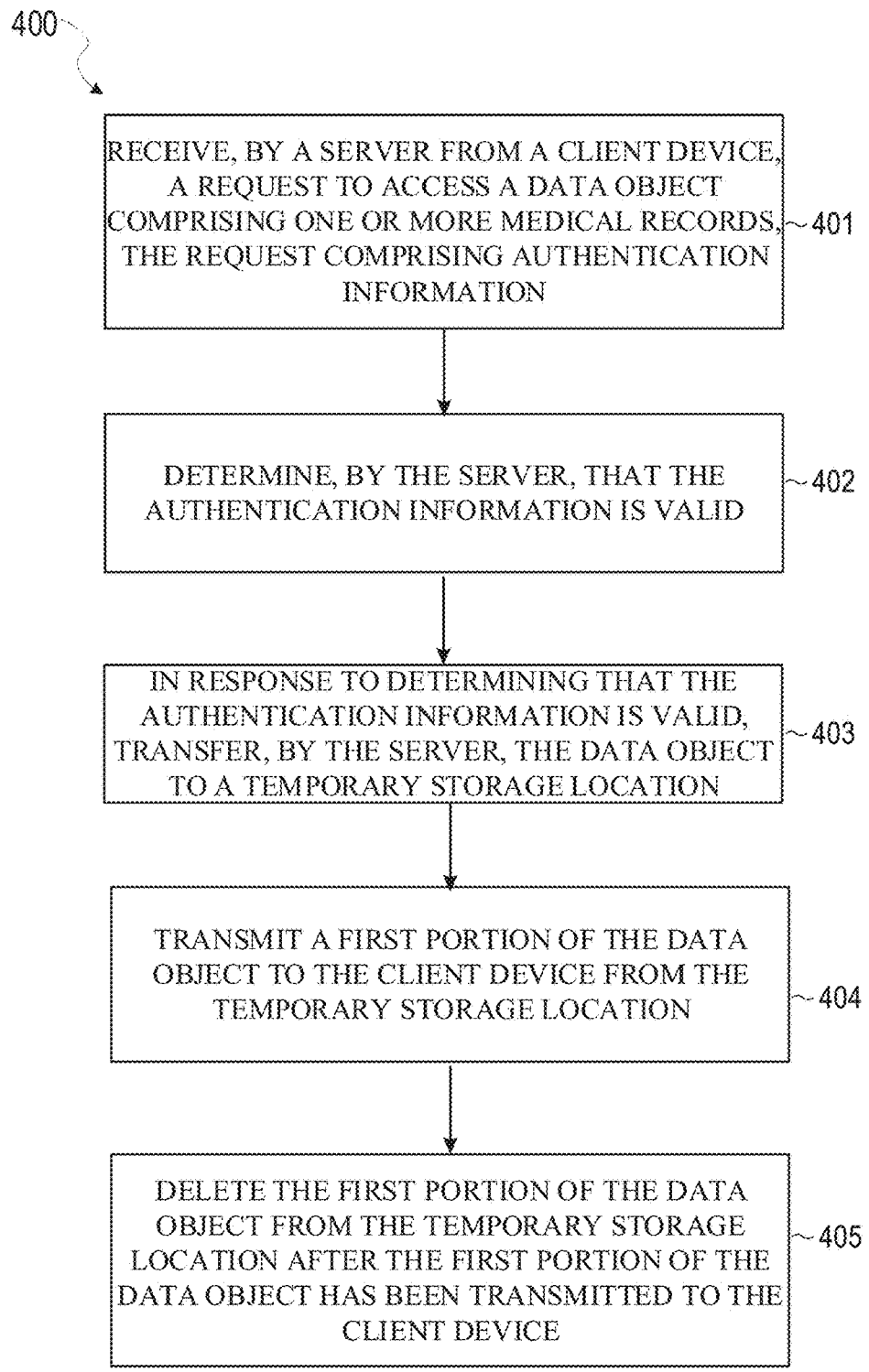
FIG. 4 is a flowchart illustrating example operations of the medical records access system, according to example embodiments.

FIG. 4 is a flowchart illustrating example operations of the medical records access system in performing process 400, according to example embodiments. The process 400 may be embodied in computer-readable instructions for execution by one or more processors such that the operations of the process 400 may be performed in part or in whole by the functional components of the system 100; accordingly, the process 400 is described below by way of example with reference thereto. However, in other embodiments, at least some of the operations of the process 400 may be deployed on various other hardware configurations. Some or all of the operations of process 400 can be in parallel, out of order, or entirely omitted.

At operation 401, the system 100 receives from a client device a request to access a data object comprising one or more medical records, the request comprising authentication information, as discussed above.

At operation 402, the system 100 determines that the authentication information is valid, as discussed above.

At operation 403, the system 100 in response to determining that the authentication information is valid, the data object is transferred to a temporary storage location, as discussed above.

At operation 404, the system 100 transmits a first portion of the data object to the client device from the temporary storage location, as discussed above.

At operation 405, the system 100 deletes the first portion of the data object from the temporary storage location after the first portion of the data object has been transmitted to the client device, as discussed above.

Figure 5:
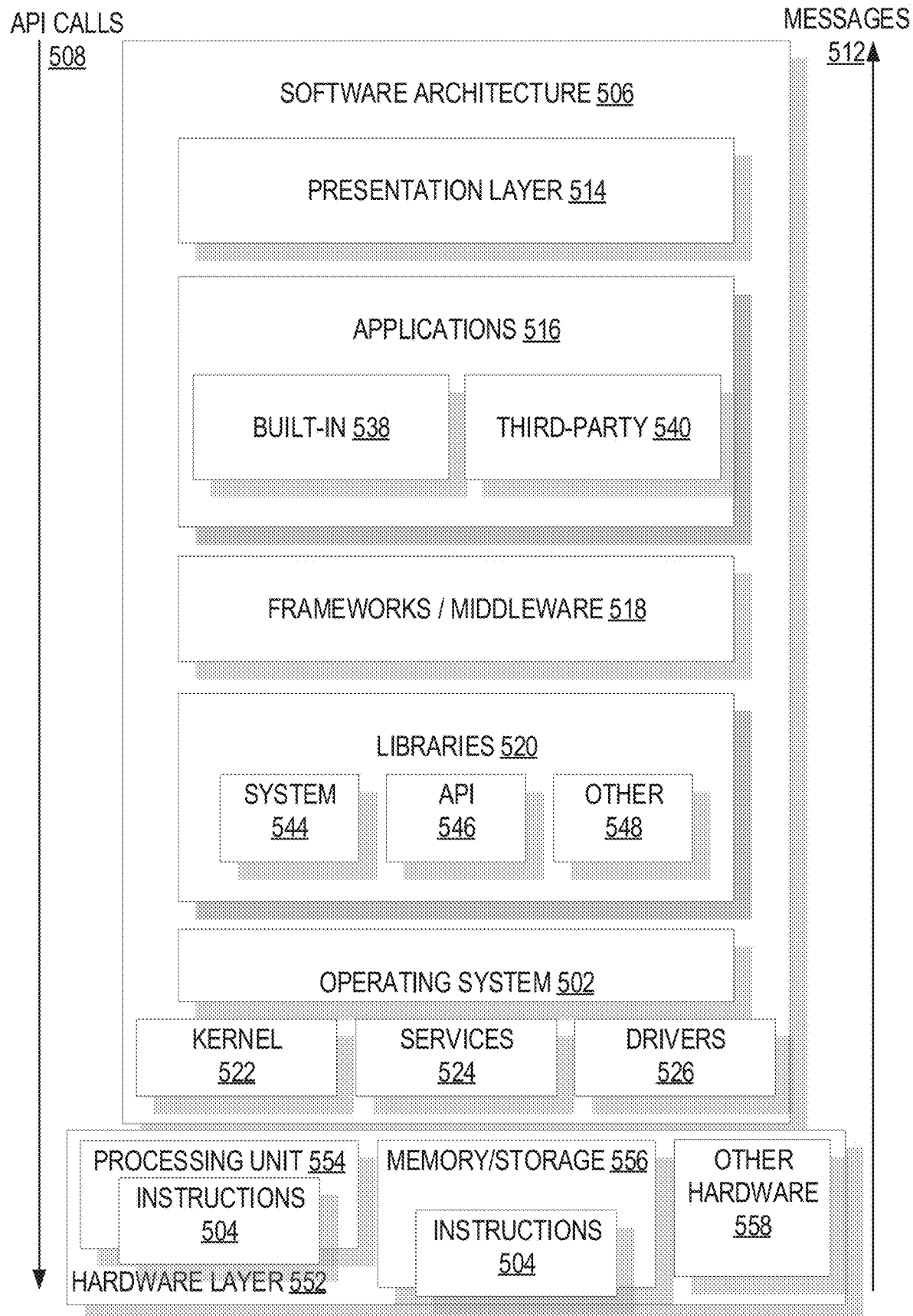
FIG. 5 is a block diagram illustrating an example software architecture, which may be used in conjunction with various hardware architectures herein described.

FIG. 5 is a block diagram illustrating an example software architecture 506, which may be used in conjunction with various hardware architectures herein described. FIG. 5 is a non-limiting example of a software architecture and it will be appreciated that many other architectures may be implemented to facilitate the functionality described herein. The software architecture 506 may execute on hardware such as machine 600 of FIG. 6 that includes, among other things, processors 604, memory 614, and input/output (I/O) components 618. A representative hardware layer 552 is illustrated and can represent, for example, the machine 600 of FIG. 6. The representative hardware layer 552 includes a processing unit 554 having associated executable instructions 504. Executable instructions 504 represent the executable instructions of the software architecture 506, including implementation of the methods, components, and so forth described herein. The hardware layer 552 also includes memory and/or storage devices memory/storage 556, which also have executable instructions 504. The hardware layer 552 may also comprise other hardware 558. The software architecture 506 may be deployed in any one or more of the components shown in FIG. 1 or 2.

In the example architecture of FIG. 5, the software architecture 506 may be conceptualized as a stack of layers where each layer provides particular functionality. For example, the software architecture 506 may include layers such as an operating system 502, libraries 520, frameworks/middleware 518, applications 516, and a presentation layer 514. Operationally, the applications 516 and/or other components within the layers may invoke API calls 508 through the software stack and receive messages 512 in response to the API calls 508. The layers illustrated are representative in nature and not all software architectures have all layers. For example, some mobile or special purpose operating systems may not provide a frameworks/middleware 518, while others may provide such a layer. Other software architectures may include additional or different layers.

The operating system 502 may manage hardware resources and provide common services. The operating system 502 may include, for example, a kernel 522, services 524, and drivers 526. The kernel 522 may act as an abstraction layer between the hardware and the other software layers. For example, the kernel 522 may be responsible for memory management, processor management (e.g., scheduling), component management, networking, security settings, and so on. The services 524 may provide other common services for the other software layers. The drivers 526 are responsible for controlling or interfacing with the underlying hardware. For instance, the drivers 526 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 520 provide a common infrastructure that is used by the applications 516 and/or other components and/or layers. The libraries 520 provide functionality that allows other software components to perform tasks in an easier fashion than to interface directly with the underlying operating system 502 functionality (e.g., kernel 522, services 524 and/or drivers 526). The libraries 520 may include system libraries 544 (e.g., C standard library) that may provide functions such as memory allocation functions, string manipulation functions, mathematical functions, and the like. In addition, the libraries 520 may include API libraries 546 such as media libraries (e.g., libraries to support presentation and manipulation of various media format such as MPREG4, H.264, MP3, AAC, AMR, JPG, PNG), graphics libraries (e.g., an OpenGL framework that may be used to render two-dimensional and three-dimensional in a graphic content on a display), database libraries (e.g., SQLite that may provide various relational database functions), web libraries (e.g., WebKit that may provide web browsing functionality), and the like. The libraries 520 may also include a wide variety of other libraries 548 to provide many other APIs to the applications 516 and other software components/devices.

The frameworks/middleware 518 (also sometimes referred to as middleware) provide a higher-level common infrastructure that may be used by the applications 516 and/or other software components/devices. For example, the frameworks/middleware 518 may provide various graphic user interface functions, high-level resource management, high-level location services, and so forth. The frameworks/middleware 518 may provide a broad spectrum of other APIs that may be utilized by the applications 516 and/or other software components/devices, some of which may be specific to a particular operating system 502 or platform.

The applications 516 include built-in applications 538 and/or third-party applications 540. Examples of representative built-in applications 538 may include, but are not limited to, a contacts application, a browser application, a book reader application, a location application, a media application, a messaging application, and/or a game application. Third-party applications 540 may include an application developed using the ANDROID™ or IOS™ software development kit (SDK) by an entity other than the vendor of the particular platform, and may be mobile software running on a mobile operating system such as IOS™, ANDROID™, WINDOWS® Phone, or other mobile operating systems. The third-party applications 540 may invoke the API calls 508 provided by the mobile operating system (such as operating system 502) to facilitate functionality described herein.

The applications 516 may use built-in operating system functions (e.g., kernel 522, services 524, and/or drivers 526), libraries 520, and frameworks/middleware 518 to create UIs to interact with users of the system. Alternatively, or additionally, in some systems, interactions with a user may occur through a presentation layer, such as presentation layer 514. In these systems, the application/component "logic" can be separated from the aspects of the application/component that interact with a user.

Figure 6:
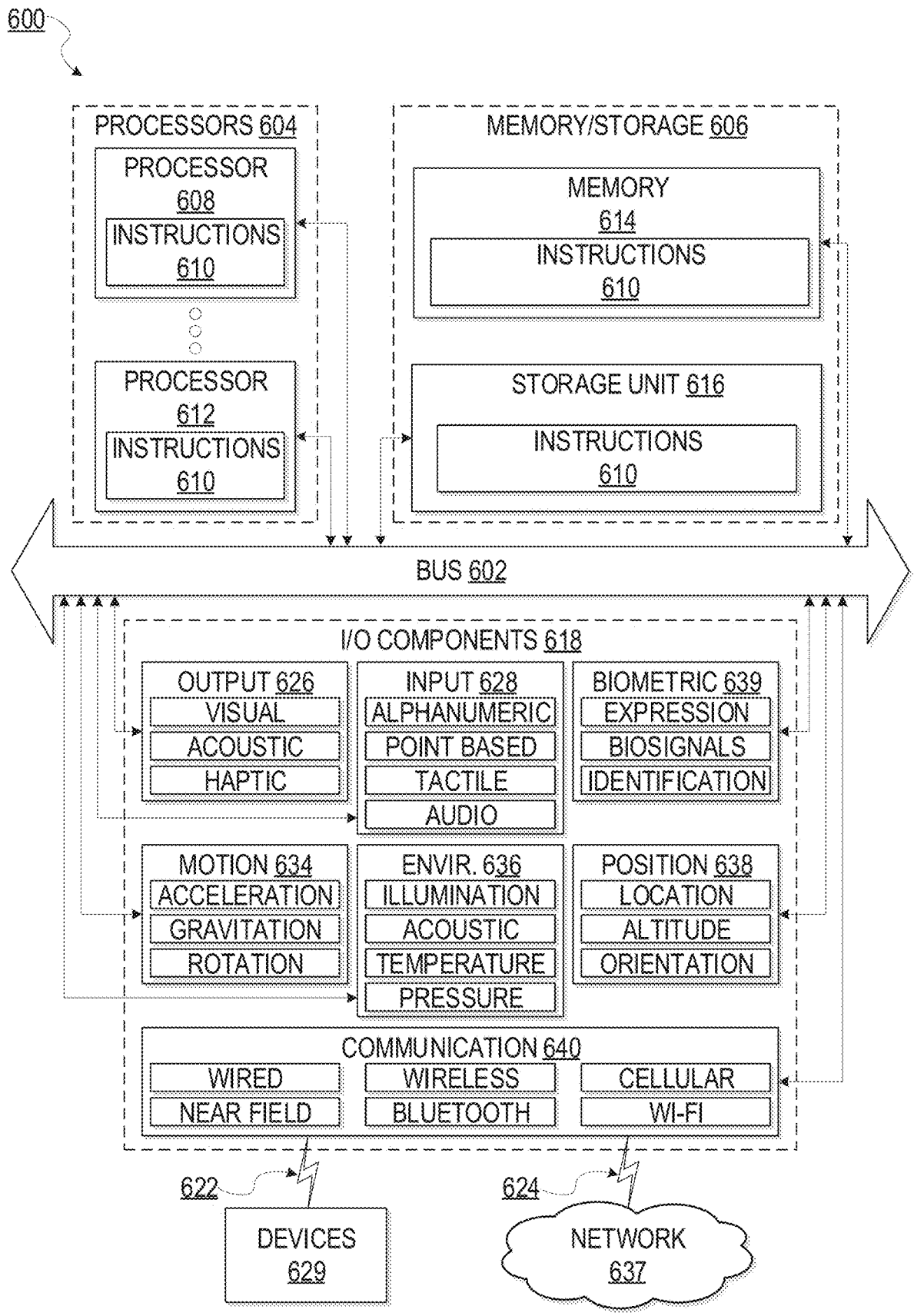
FIG. 6 is a block diagram illustrating components of a machine, according to some example embodiments.

FIG. 6 is a block diagram illustrating components of a machine 600, according to some example embodiments, able to read instructions from a machine-readable medium (e.g., a machine-readable storage medium) and perform any one or more of the methodologies discussed herein. Specifically, FIG. 6 shows a diagrammatic representation of the machine 600 in the example form of a computer system, within which instructions 610 (e.g., software, a program, an application, an applet, an app, or other executable code) for causing the machine 600 to perform any one or more of the methodologies discussed herein may be executed.

As such, the instructions 610 may be used to implement devices or components described herein. The instructions 610 transform the general, non-programmed machine 600 into a particular machine 600 programmed to carry out the described and illustrated functions in the manner described. In alternative embodiments, the machine 600 operates as a standalone device or may be coupled (e.g., networked) to other machines. In a networked deployment, the machine 600 may operate in the capacity of a server machine (gateway) or a client machine in a server-client network environment, or as a peer machine in a peer-to-peer (or distributed) network environment. The machine 600 may comprise, but not be limited to a server computer, a client computer, a personal computer (PC), a tablet computer, a laptop computer, a netbook, a STB, a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 610, sequentially or otherwise, that specify actions to be taken by machine 600. Further, while only a single machine 600 is illustrated, the term "machine" shall also be taken to include a collection of machines that individually or jointly execute the instructions 610 to perform any one or more of the methodologies discussed herein.

The machine 600 may include processors 604, memory/storage 606, and I/O components 618, which may be configured to communicate with each other such as via a bus 602. In an example embodiment, the processors 604 (e.g., a central processing unit (CPU), a reduced instruction set computing (RISC) processor, a complex instruction set computing (CISC) processor, a graphics processing unit (GPU), a digital signal processor (DSP), an application-specific integrated circuit (ASIC), a radio-frequency integrated circuit (RFIC), another processor, or any suitable combination thereof) may include, for example, a processor 608 and a processor 612 that may execute the instructions 610. The term "processor" is intended to include multi-core processors 604 that may comprise two or more independent processors (sometimes referred to as "cores") that may execute instructions contemporaneously. Although FIG. 6 shows multiple processors 604, the machine 600 may include a single processor with a single core, a single processor with multiple cores (e.g., a multi-core processor), multiple processors with a single core, multiple processors with multiple cores, or any combination thereof.

The memory/storage 606 may include a memory 614, such as a main memory, or other memory storage, database 110, and a storage unit 616, both accessible to the processors 604 such as via the bus 602. The storage unit 616 and memory 614 store the instructions 610 embodying any one or more of the methodologies or functions described herein. The instructions 610 may also reside, completely or partially, within the memory 614, within the storage unit 616, within at least one of the processors 604 (e.g., within the processor's cache memory), or any suitable combination thereof, during execution thereof by the machine 600. Accordingly, the memory 614, the storage unit 616, and the memory of processors 604 are examples of machine-readable media.

The I/O components 618 may include a wide variety of components to receive input, provide output, produce output, transmit information, exchange information, and capture measurements. The specific I/O components 618 that are included in a particular machine 600 will depend on the type of machine. For example, portable machines such as mobile phones will likely include a touch input device or other such input mechanisms, while a headless server machine will likely not include such a touch input device. It will be appreciated that the I/O components 618 may include many other components that are not shown in FIG. 6. The I/O components 618 are grouped according to functionality merely for simplifying the following discussion and the grouping is in no way limiting. In various example embodiments, the I/O components 618 may include output components 626 and input components 628. The output components 626 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 628 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 618 may include biometric components 639, motion components 634, environmental components 636, or position components 638 among a wide array of other components. For example, the biometric components 639 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 634 may include acceleration sensor components (e.g., accelerometer), gravitation sensor components, rotation sensor components (e.g., gyroscope), and so forth. The environmental components 636 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 638 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 618 may include communication components 640 operable to couple the machine 600 to a network 637 or devices 629 via coupling 624 and coupling 622, respectively. For example, the communication components 640 may include a network interface component or other suitable device to interface with the network 637. In further examples, communication components 640 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 629 may be another machine or any of a wide variety of peripheral devices (e.g., a peripheral device coupled via a USB).

Moreover, the communication components 640 may detect identifiers or include components operable to detect identifiers. For example, the communication components 640 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 640, such as location via Internet Protocol (IP) geo-location, location via Wi-Fi® signal triangulation, location via detecting a NFC beacon signal that may indicate a particular location, and so forth.

Glossary

"CARRIER SIGNAL" in this context refers to any intangible medium that is capable of storing, encoding, or carrying transitory or non-transitory instructions for execution by the machine, and includes digital or analog communications signals or other intangible medium to facilitate communication of such instructions. Instructions may be transmitted or received over the network using a transitory or non-transitory transmission medium via a network interface device and using any one of a number of well-known transfer protocols.

"CLIENT DEVICE" in this context refers to any machine that interfaces to a communications network to obtain resources from one or more server systems or other client devices. A client device may be, but is not limited to, a mobile phone, desktop computer, laptop, PDA, smart phone, tablet, ultra book, netbook, laptop, multi-processor system, microprocessor-based or programmable consumer electronics, game console, set-top box, or any other communication device that a user may use to access a network.

"COMMUNICATIONS NETWORK" in this context refers to one or more portions of a network that may be an ad hoc network, an intranet, an extranet, a virtual private network (VPN), a LAN, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

"MACHINE-READABLE MEDIUM" in this context refers to a component, device, or other tangible media able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

"COMPONENT" or "MODULE" in this context refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an ASIC. A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"PROCESSOR" in this context refers to any circuit or virtual circuit (a physical circuit emulated by logic executing on an actual processor) that manipulates data values according to control signals (e.g., "commands," "op codes," "machine code," etc.) and which produces corresponding output signals that are applied to operate a machine. A processor may, for example, be a CPU, a RISC processor, a CISC processor, a GPU, a DSP, an ASIC, a RFIC, or any combination thereof. A processor may further be a multi-core processor having two or more independent processors (sometimes referred to as "cores") that may execute instructions contemporaneously.

Changes and modifications may be made to the disclosed embodiments without departing from the scope of the present disclosure. These and other changes or modifications are intended to be included within the scope of the present disclosure, as expressed in the following claims.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
   receiving, by one or more processors of a server from a client device, a request to access a data object comprising one or more medical records, the request comprising authentication information;
   determining, by the server, that the authentication information is valid;
   in response to determining that the authentication information is valid, transferring, by the server, the data object to a temporary storage location that is remote from the client device and that is remote from the server;
   causing transmission of a first portion of the data object to the client device from the temporary storage location; and
   causing deletion of the first portion of the data object from the temporary storage location that is remote from the client device and that is remote from the server after the first portion of the data object has been transmitted to the client device.

2. The method of claim 1, further comprising deleting the data object from the temporary storage location after a threshold period of time elapses from when the request is received by the server.

3. The method of claim 1, wherein the server comprises a content delivery network, and wherein the authentication information is generated by:
   receiving, from a healthcare application installed on the client device, patient information by a secure healthcare entity, the secure healthcare entity being a third-party relative to an entity associated with the healthcare application; and
   transmitting an authentication token by the secure healthcare entity to the healthcare application.

4. The method of claim 3, further comprising:
   providing a list of medical records associated with the patient to the healthcare application; and
   causing the list of medical records to be displayed on a user interface of the healthcare application.

5. The method of claim 4, further comprising:
   detecting selection of the one or more medical records from the list of medical records; and
   retrieving a document reference uniform resource locator associated with the one or more medical records.

6. The method of claim 5, wherein the healthcare application provides the authentication token and the document reference uniform resource locator to the server as part of the request.

7. The method of claim 6, further comprising:
   accessing issuer information contained in the token in response to receiving the request; and
   determining that the issuer information matches a known issuer of the token to determine that the authentication information is valid.

8. The method of claim 6, further comprising:
   accessing identity information contained in the token; and
   applying one or more rules to the identity information to determine that the authentication information is valid.

9. The method of claim 1, wherein the one or more medical records comprise X-ray images, DICOM files or magnetic resonance images.

10. The method of claim 1, wherein a file size of the one or more medical records exceeds a file size transfer limit of a cloud computing storage server associated with a secure healthcare entity that maintains secure access to the one or more medical records, the file size transfer limit corresponding to a file size exchange protocol between the cloud computing storage server and a healthcare application installed on the client device.

11. The method of claim 1, wherein a file size of the one or more medical records exceeds a file size transfer limit of the server, the file size transfer limit corresponding to a file size exchange protocol between the storage and an application installed on the client device.

12. The method of claim 1, wherein the first portion comprises a first medical record, further comprising:
retaining a second portion of the data object comprising a second medical record on the temporary storage location after deleting the first portion of the data object.

13. The method of claim 12, wherein the second portion of the data object is automatically deleted after a threshold period of time.

14. A system comprising:
one or more processors coupled to a memory comprising non-transitory computer instructions that, when executed by the one or more processors, perform operations comprising:
receiving, by a server from a client device, a request to access a data object comprising one or more medical records, the request comprising authentication information;
determining, by the server, that the authentication information is valid;
in response to determining that the authentication information is valid, transferring, by the server, the data object to a temporary storage location that is remote from the client device and that is remote from the server;
causing transmission of a first portion of the data object to the client device from the temporary storage location; and
causing deletion of the first portion of the data object from the temporary storage location that is remote from the client device and that is remote from the server after the first portion of the data object has been transmitted to the client device.

15. The system of claim 14, wherein the operations further comprise deleting the data object from the temporary storage location after a threshold period of time elapses from when the request is received by the server.

16. The system of claim 14, wherein the server comprises a content delivery network, and wherein the authentication information is generated by:
receiving, from a healthcare application installed on the client device, patient information by a secure health entity, the secure health entity being a third-party relative to an entity associated with the healthcare application; and
transmitting an authentication token by the secure health entity to the healthcare application.

17. The system of claim 16, wherein the operations further comprise:
providing a list of medical records associated with the patient to the healthcare application; and
causing the list of medical records to be displayed on a user interface of the healthcare application.

18. The system of claim 17, wherein the operations further comprise:
detecting selection of the one or more medical records from the list of medical records; and
retrieving a document reference uniform resource locator associated with the one or more medical records.

19. The system of claim 18, wherein the healthcare application provides the authentication token and the document reference uniform resource locator to the server as part of the request.

20. A non-transitory computer readable medium comprising non-transitory computer-readable instructions for performing operations comprising:
receiving, by a server from a client device, a request to access a data object comprising one or more medical records, the request comprising authentication information;
determining, by the server, that the authentication information is valid;
in response to determining that the authentication information is valid, transferring, by the server, the data object to a temporary storage location that is remote from the client device and that is remote from the server;
causing transmission of a first portion of the data object to the client device from the temporary storage location; and
causing deletion of the first portion of the data object from the temporary storage location that is remote from the client device and that is remote from the server after the first portion of the data object has been transmitted to the client device.

* * * * *